(12) United States Patent
Toyoda et al.

(10) Patent No.: US 7,445,890 B1
(45) Date of Patent: Nov. 4, 2008

(54) UCP-2 PROMOTER AND USE THEREOF

(75) Inventors: Yukio Toyoda, Hyogo (JP); Makoto Kobayashi, Hyogo (JP); Shigeru Igaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/869,098

(22) PCT Filed: Dec. 22, 1999

(86) PCT No.: PCT/JP99/07198

§ 371 (c)(1),
(2), (4) Date: Sep. 20, 2001

(87) PCT Pub. No.: WO00/39315

PCT Pub. Date: Jul. 6, 2000

(30) Foreign Application Priority Data

Dec. 24, 1998 (JP) .................................. 10-366719

(51) Int. Cl.
*C12Q 1/68* (2006.01)
*C12N 5/00* (2006.01)
*C12N 15/00* (2006.01)
*C07H 21/04* (2006.01)

(52) U.S. Cl. .................. 435/6; 435/320.1; 435/325; 435/375; 435/455; 536/23.1; 536/24.2

(58) Field of Classification Search .............. 435/6, 435/325, 455, 320.1, 69.1, 29; 536/23.1, 536/24.1
See application file for complete search history.

(56) References Cited

U.S. PATENT DOCUMENTS

| 5,807,740 A | 9/1998 | Amaral et al. |
| 5,849,514 A | 12/1998 | Amaral et al. |
| 2003/0119775 A1 * | 6/2003 | Surwit et al. .................. 514/44 |

FOREIGN PATENT DOCUMENTS

WO  WO 98/31396  * 7/1998

OTHER PUBLICATIONS

Lewin, Genes V, Oxford University Press and Cell Press, pp. 767-796, copyright 1994.*
GenBank Accession No. NM_003355.*
Stratagene catalog. 1988, Gene characterization Kits Table of Contents. p. 39.*
Diabetes vol. 46, May 900-906 (1997).
Nature Genet, vol. 15, March, 269-272 (1997).
Biochem. Biophys. Res. Commun. vol. 244, No. 1, 75-78 (1998).
Biochem. Biophys. Res. Commun. vol. 265, No. 2, 326-334 (1999).
Cortez-Pinto, H. et al., "Bacterial lipopolysaccharide induces uncoupling protein-2 expression in hepatocytes by a tumor necrosis factor-alpha-dependent mechanism." Biochem Biophys Res Commun. Oct. 9, 1998; 251(1):313-9.
Yamada, M. et al., "Genomic organization and promoter function of the mouse uncoupling protein-2 (UCP2) gene." FEBS Lett., Jul. 31, 1998; 432(1-2):65-9.
Bouillaud, F. et al., "Uncoupling protein-2, UCP2 gene clone hUCP2-g2", Nov. 24, 1998, Database EMBL Online!, Database Accession No. AAV44599, Abstract of WO 9831396-A1.
Kelly, LJ. et al., "Peroxisome proliferator-activated receptors gamma and alpha mediate in vivo regulation of uncoupled protein (UCP-1, UCP-2, UCP-3) gene expression." Endocrinology Dec. 1998; 139(12): 4920-4927.
Yubero, P. et al., "Identification of tissue-specific protein binding domains in the 5'-proximal regulatory region of the rat mitochondrial brown fat uncoupling protein gene." Biochemical and Biophysical Research Communications, 1994; 204(2): 867-873.
Jezek, P. et al., "Mammalian mitochondrial uncoupling proteins.", International Journal of Biochemistry and Cell Biology, Nov. 1998; 30(11): 1163-1168.

* cited by examiner

*Primary Examiner*—Sumesh Kaushal
(74) *Attorney, Agent, or Firm*—David G. Conlin; Kathryn A. Piffat; Edwards Angell Palmer & Dodge LLP

(57) ABSTRACT

This invention relates to a DNA containing uncoupling protein-2 (UCP-2) promoter region containing the regulator sequence, a transformant transformed with the DNA, a method for screening a compound or its salt that promotes or inhibits UCP-2 promoter activity characterized by use of the transformant, a method for screening an antiobestic drug, an antidiabetic drug, a depressor, an antihyperlipemic drug, and an antipyretic drug characterized by use of the transformant, a kit for screening a compound or its salt that promotes or inhibits UCP-2 promoter activity characterized by use of the transformant, and pharmaceutical composition containing a compound or its salt that promotes or inhibits UCP-2 promoter activity obtained using the screening method or the screening kit.

3 Claims, 10 Drawing Sheets

```
          10         20         30         40         50         60
     AACGGATCTG CCCGCCTCAG CCTCCCAAAG TGCTGGGATT GCAGGCGTGA GCCACCTCAC 70         80         90        100        110        120
     CTGGCTACAA GTTTTCAAAA TACATTTATC TAGTACCCAT ACATTCTCCA GTTTGTCCAC 130        140        150        160        170        180
     AGGACATCTT ATGACTTGAG CAAGCTGCTA AAAATCCAAG GGTGCAGCGT TTGTATGTCT 190        200        210        220        230        240
     ATAGGATTGC TCAGATCTGC CCCCACCCTG AAAGAATTTA AGAGAATTTC TTGAGGCCAG 250        260        270        280        290        300
     GCACAGTGGC TCACACCTGT AATTCCAGTA CTGTGAGAGT CCGAGGTCAG AGGACTGCTT
                                                     PPRE 310        320        330        340        350        360
     GAGGCCAGGA GTTCAAGAGC AGCCTGGACA ACACAGGGAG ACCTGTCACT ACAAAGAATA 370        380        390        400        410        420
     AATAAATTAG CCAGGCTTAG TGGCTCATCC CTGTGGTCCC AGCTACTAGG GAGGCAGAAG 430        440        450        460        470        480
     TAGGACTGCT TGTCCCAGGA GGTCAAGACT GCAGTGAGCT GAGACCCAGC CACCTGCATT
         490        500        510        520        530        540

CCAGCCTGGG CAACAAAAAG AGACCCTGTC TCAAAAAATA AGTTAAATAA ATAAATAATA
         550        560        570        580        590        600

AAAATAGTTT AAACCCTAAA CACATCTTCT TTTTCAAAGA GGACTTCTTA AGGACTTCAT 610        620        630        640        650        660
     GCTGCGTCCT GTTGATCTCC ACTTCCCTTT TTCAGCGTCC ACACTTTTAA CAGTCTCTTT
```

FIG. IA

```
       670        680        690        700        710        720
TGCCAAGGAT AATAAGTATA TAGTTTCTGG AATCCAGATT CTTCCCTGTT TGGACAGCCA 730        740        750        760        770        780
GGGGGACAAT TTTTGGTCTG CAGGCCTTTG CATCTGTTCT GCTGTTGCTC AGCAATCTCA
                                     GRE
       790        800        810        820        830        840
CAGCAAATTT GCCGAGCCTC TCCGGAATGC ACAGCCAGAC AGAGCTCAGC GCAAAAGCTA 850        860        870        880        890        900
GAGAACCTGG CGGAGGGAGA CTCACAGTGC CACAAAAAAA CTTTATCTTT TCTTTTTTT 910        920        930        940        950        960
TTTCTTTTCT TTCTTTCTCT TTCTTTCTTG TCTTTCTGTC TTTCCTCTCT CTCTCTCTGT 970        980        990       1000       1010       1020
CTTTCTTTCC TCTCTTTCTT TCTTTTTTCC TACATGGCAA GATCTCCTCA TGGCAGAAAT 1030       1040       1050       1060       1070       1080
AATCTGCCTT GACTTCTGTT TCCACGCTGC TTCTGCCAGG ACCATGCGCT CGGCGTGTTT
 GRE
      1090       1100       1110       1120       1130       1140
TTCTTTCCGC TATAATTATC CAGGCCCATC CCAGCTCTGG TCCCCTCAGC TGTTCCCTGG 1150       1160       1170       1180       1190       1200
CAGTCCCTTC TGCTGGTGAA AACACATATG GCGCCGGCCT GACCAGGGTG TAAGTGTGTG 1210       1220       1230       1240       1250       1260
AATATCAGGA AGATGACTGA ACGTCTTTGG GACTCCGTTT CCTCATTGTA AAATGGAGGT
```

FIG. 1B

```
       1270       1280       1290       1300       1310       1320
TAATACCAGC CTTCTTCTAC TCCCCAAACG CACGTGTTTG TCCCGGCCAG AGGGCCCAAT
                                                           C/EBP 1330       1340       1350       1360       1370       1380
TGTTGGCTGT TCACGCATCA GTTACCCCCA CAGGACGGGT CAGCCAATTA AAGGCGAACC
                                                C/EBP 1390       1400       1410       1420       1430       1440
AGGCCCGGTC CATCTCCTGA CGCCTTTTCT CATCCCAGGG CTGGACAGGC AGCTGGCCTG
                                                           MyoD 1450       1460       1470       1480       1490       1500
GGCCCGGCTC TGCCTTGTCA CGTGCGGGGG CCGGCCCGTT TGCTTGTCTG TGTGTAGGAG
           GRE 1510       1520       1530       1540       1550       1560
CGTGAGGTCA CGCTGGGTGC TCCCGCCCCG CCGGGGCCTT TAGTGTCCCT GGTCCCTAAA 1570       1580       1590       1600       1610       1620
CGCCAGGCCG CTCCACCGGG GGAGAAGGCG CGAACCCCAG CCGAGCCCAA CGGCTGTTGT 1630       1640       1650       1660       1670       1680
CGGTTGCCGG GCCACCTGTT GCTGCAGTTC TGATTGGTTC CTTCCCCCGA CAACGCGGCG 1690       1700       1710       1720       1730       1740
GCTGTAACCA ATCGACAGCG AGGCCGGTCG CGAGGCCCCA GTCCCGCCCT GCAGGAGCCA
       C/EBP 1750       1760       1770       1780       1790       1800
GCCGCGCGCT CGCTCGCAGG AGGGTGGGTA GTTTGCCCAG CGTAGGGGGG CTGGGCCCAT 1810       1820       1830       1840       1850       1860
AAAAGAGGAA GTGCACTTAA GACACGGCCC CGCTGGACGC TTGTTAGAAA CCGTCCTGGC 1870       1880       1890       1900       1910       1920
TGGGAAGGCA AGAGGTGTGT GACTGGACAA GACTTGTTTC TCGCGGTCAG TCTTGCCATC
```

FIG. IC

```
         1930       1940       1950       1960       1970       1980
     CTCACAGAGG TTGGCGGCCC GAGAGAGTGT GAGGCAGAGG CGGGGAGTGG CAAGGGAGTG 1990       2000       2010       2020       2030       2040
     ACCATCTCGG GGAACGAAGG AGTAAACGCG GTGATGGGAC GCACGGAAAC GGGAGTGGAG 2050       2060       2070       2080       2090       2100
     AAAGTCATGG AGAGAACCCT AGGCGGGGCG GTCCCCGCGG AAAGGCGGCT GCTCCAGGGT 2110       2120       2130       2140       2150       2160
     CTCCGCACCC AAGTAGGAGC TGGCAGGCCC GGCCCCGCCC CGCAGGCCCC ACCCCGGGCC 2170       2180       2190       2200       2210       2220
     CCGCCCCCGA GGCTTAAGCC GCGCCGCCGC CTGCGCGGAG CCCCACTGCG AAGCCCAGCT 2230       2240       2250       2260       2270       2280
     GCGCGCGCCT TGGGATTGAC TGTCCACGCT CGCCCGGCTC GTCCGACGCG CCCTCCGCCA 2290       2300       2310       2320       2330       2340
     GCCGACAGAC ACAGCCGCAC GCACTGCCGT GTTCTCCCTG CGGCTCGGTG AGCCTGGCCC 2350       2360       2370       2380       2390       2400
     CAGCCCTGCG CCCTTTGCGC CCCCCACGCT TGTTCTGCGT GCGCTGCCCG CTCTTCCATT 2410       2420       2430       2440       2450       2460
     TACCTTCTCT CCCACCCAAG TTTGTACTCT TTTCTTTCTC TCGGTTTTAT TTTTTGTTTT 2470       2480       2490       2500       2510       2520
     TGTTTGTTTG TTTGAGACAG GCTTTCGCTC TGTCTCCCAG GCTGGAGTGC AGTGGCGCGA 2530       2540       2550       2560       2570       2580
     TCTCGGCTCA CTGCAGCCTC CACCTCCCAG GTTCAAGCGA TCCGCCTGCC GAGTAGCTGG
```

FIG. 1D

```
     2590       2600       2610       2620       2630       2640
GATTACAGGC GCCCGCCACC ACGCCTGGCT AATTTTTGTG TTTTGTAGAG ATGGGGTTTC 2650       2660       2670       2680       2690       2700
GCCATGTTGG CCAGGCTGGC CTCGAACTGC TCAGCTCAAG CAATCCGCCC GCCTCGGCCT 2710       2720       2730       2740       2750       2760
CACAAAGTCC TAGAATTTTA GGCATGAGCC TCCGGGTCCG GCCTGTGCTA ATCCTTTCTG 2770       2780       2790       2800       2810       2820
TCCTTGGTTC TTTATTTCCC TTCTCTCTTT TTCTTAGTCC CTTTTGTTCT TTCCCTCTCC 2830       2840       2850       2860       2870       2880
CGTTCAGTTG GCTGTCGTTT GAGCCTCCAC CTTTTCACTC CCTCCTTTCC ACCACGATGC 2890       2900       2910       2920       2930       2940
CGAGCCCTGC CTTGGATGGG GACCATCAGC GATGACCACA ATGACCTCTC CCTTACCAGG 2950       2960       2970       2980       2990       3000
CAGCTCCAGG CAGTGTTCCT GCACCGCCTT TCCCAAGGCT TGGGGGCTTT TTCTAGTGGG 3010       3020       3030       3040       3050       3060
CTTTGAGCTG CTCAATCTGG CCTCTGCAGG GCCGGCTCCC AGCCCTTCCA ACCTCCTCAC 3070       3080       3090       3100       3110       3120
AGCCCGACCT GGGACCTAGC CAATTCCCGG AGAGTCTCTG TCCCATCGTG ACCCCCTCAC 3130       3140       3150       3160       3170       3180
AACTCTCCCA CTCACCAAAG TCTGATGACT GTGCTAGGGG GTGCTTATAT AGAGTACTGA 3190       3200       3210       3220       3230       3240
GTGTTACAAA AGCAGAAGTC TGGATGAGAA CCAATTTGTG ATATTAAGCA GGTGGGGTGG
```

FIG.1E

```
       3250       3260       3270       3280       3290       3300
GGGTGGGGAG TGTACCTAGG TTCATTTTCC GCCCTGCTTT TCCCCTTTCC AGTGTGTGCA 3310       3320       3330       3340       3350       3360
CTTAACCAGT CCCTGGGCCC TGTTCCCCAT CCCCCTCCAA GGCATGGATT GGGTGGGCTT 3370       3380       3390       3400       3410       3420
GTGTGTCTTG GGGCAGGTGG CCCTTTCTAA ACTCTCTGCC TTTGCTCACC CACAGGACAC 3430       3440       3450       3460       3470       3480
ATAGTATGAC CATTAGGTGT TTCGTCTCCC ACCCATTTTC TATGGAAAAC CAAGGGGATC 3490       3500       3510       3520       3530       3540
GGGCCATGAT AGCCACTGGC AGCTT         (SEQ ID NO:1)
```

FIG. IF

SEQUENCE LISTING

<160> NUMBER OF SEQ ID NOS: 5

<210> SEQ ID NO 1
<211> LENGTH: 3505
<212> TYPE: DNA
<213> ORGANISM: Human

<400> SEQUENCE: 1

```
aacggatctg cccgcctcag cctcccaaag tgctgggatt gcaggcgtga gccacctcac      60
ctggctacaa gttttcaaaa tacatttatc tagtacccat acattctcca gtttgtccac     120
aggacatctt atgacttgag caagctgcta aaaatccaag ggtgcagcgt ttgtatgtct     180
ataggattgc tcagatctgc ccccaccctg aaagaattta agagaatttc ttgaggccag     240
gcacagtggc tcacacctgt aattccagta ctgtgagagt ccgaggtcag aggactgctt     300
gaggccagga gttcaagagc agcctggaca acacagggag acctgtcact acaaagaata     360
aataaattag ccaggcttag tggctcatcc ctgtggtccc agctactagg gaggcagaag     420
taggactgct tgtcccagga ggtcaagact gcagtgagct gagacccagc cacctgcatt     480
ccagcctggg caacaaaaag agaccctgtc tcaaaaaata agttaaataa ataaataata     540
aaaatagttt aaaccctaaa cacatcttct ttttcaaaga ggacttctta aggacttcat     600
gctgcgtcct gttgatctcc acttcccttt ttcagcgtcc acacttttaa cagtctcttt     660
```

-continued

```
tgccaaggat aataagtata tagtttctgg aatccagatt cttccctgtt tggacagcca      720
gggggacaat ttttggtctg caggcctttg catctgttct gctgttgctc agcaatctca      780
cagcaaattt gccgagcctc tccggaatgc acagccagac agagctcagc gcaaaagcta      840
gagaacctgg cggagggaga ctcacagtgc cacaaaaaaa ctttatcttt tcttttttt       900 tttcttttct ttctttctct ttctttcttg tctttctgtc tttcctctct ctctctctgt      960
ctttctttcc tctctttctt tcttttttcc tacatggcaa gatctcctca tggcagaaat     1020
aatctgcctt gacttctgtt ccacgctgc ttctgccagg accatgcgct cggcgtgttt      1080
ttctttccgc tataattatc caggcccatc ccagctctgg tccctcagc tgttccctgg      1140 cagtccttc tgctggtgaa aacacatatg gcgccggcct gaccagggtg taagtgtgtg      1200
aatatcagga agatgactga acgtctttgg gactccgttt cctcattgta aaatggaggt     1260
taataccagc cttcttctac tccccaaacg cacgtgtttg tcccggccag agggcccaat    1320
tgttggctgt tcacgcatca gttaccccca caggacgggt cagccaatta aaggcgaacc    1380
aggcccggtc catctcctga cgccttttct catcccaggg ctggacaggc agctggcctg    1440
ggcccggctc tgccttgtca cgtgcggggg ccggcccgtt tgcttgtctg tgtgtaggag   1500
cgtgaggtca cgctgggtgc tcccgccccg ccggggcctt tagtgtccct ggtccctaaa    1560
cgccaggccg ctccaccggg ggagaaggcg cgaaccccag ccgagcccaa cggctgttgt    1620
cggttgccgg gccacctgtt gctgcagttc tgattggttc cttcccccga caacgcggcg   1680
gctgtaacca atcgacagcg aggccggtcg cgaggcccca gtcccgccct gcaggagcca   1740
gccgcgcgct cgctcgcagg agggtgggta gtttgcccag cgtaggggg ctgggcccat    1800 aaaagaggaa gtgcacttaa gacacggccc cgctggacgc ttgttagaaa ccgtcctggc    1860
tgggaaggca agaggtgtgt gactggacaa gacttgtttc tggcggtcag tcttgccatc   1920
ctcacagagg ttggcggccc gagagagtgt gaggcagagg cggggagtgg caagggagtg   1980
accatctcgg ggaacgaagg agtaaacgcg gtgatgggac gcacggaaac gggagtggag   2040
aaagtcatgg agagaaccct aggcggggcg gtccccgcgg aaaggcggct gctccagggt   2100
ctccgcaccc aagtaggagc tggcaggccc ggccccgccc cgcaggcccc accccgggcc   2160
ccgcccccga ggcttaagcc gcgccgccgc ctgcgcggag ccccactgcg aagcccagct   2220
gcgcgcgcct tgggattgac tgtccacgct cgccggctc gtccgacgcg ccctccgcca   2280
gccgacagac acagccgcac gcactgccgt gttctccctg cggctcggtg agcctggccc   2340
cagccctgcg ccctttgcgc ccccacgct tgttctgcgt gcgctgcccg ctcttccatt    2400
taccttctct cccacccaag tttgtactct ttctctctc tcggttttat tttttgtttt   2460
tgtttgtttg tttgagacag gctttcgctc tgtctcccag gctggagtgc agtggcgcga   2520
tctcggctca ctgcagcctc cacctcccag gttcaagcga tccgcctgcc gagtagctgg   2580
gattacaggc gcccgccacc acgcctggct aattttttgtg ttttgtagag atggggtttc   2640
gccatgttgg ccaggctggc ctcgaactgc tcagctcaag caatccgccc gcctcggcct   2700
cacaaagtcc tagaatttta ggcatgagcc tccgggtccg gcctgtgcta atcctttctg   2760
tccttggttc tttatttccc ttctctcttt ttcttagtcc cttttgttct ttccctctcc   2820
cgttcagttg gctgtcgttt gagcctccac cttttcactc cctcctttcc accacgatgc   2880
cgagccctgc cttggatggg gaccatcagc gatgaccaca atgacctctc ccttaccagg   2940
cagctccagg cagtgttcct gcaccgcctt tcccaaggct tggggctttt ttctagtggg   3000 cttttgagctg ctcaatctgg cctctgcagg gccggctccc agcccttcca acctcctcac   3060
```

-continued

```
agcccgacct gggacctagc caattcccgg agagtctctg tcccatcgtg acccctcac      3120 aactctccca ctcaccaaag tctgatgact gtgctagggg gtgcttatat agagtactga      3180
gtgttacaaa agcagaagtc tggatgagaa ccaatttgtg atattaagca ggtggggtgg      3240
gggtggggag tgtacctagg ttcattttcc gccctgcttt tccccttttcc agtgtgtgca      3300 cttaaccagt ccctgggccc tgttccccat cccctccaa ggcatggatt gggtgggctt       3360
gtgtgtcttg gggcaggtgg ccctttctaa actctctgcc tttgctcacc cacaggacac      3420
atagtatgac cattaggtgt ttcgtctccc acccattttc tatggaaaac caagggatc       3480 gggccatgat agccactggc agctt                                            3505

<210> SEQ ID NO 2
<211> LENGTH: 30
<212> TYPE: DNA
<213> ORGANISM: artificial sequence
<220> FEATURE:
<223> OTHER INFORMATION: primer

<400> SEQUENCE: 2
atggttgggt tcaaggccac agatgtgccc                                        30

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3
atacaggccg atgcggacag aggcaaagct                                        30

<210> SEQ ID NO 4
<211> LENGTH: 28
<212> TYPE: DNA
<213> ORGANISM: artificial sequence
<220> FEATURE:
<223> OTHER INFORMATION: primer

<400> SEQUENCE: 4
caaagctgcc agtggctatc atggcccg                                          28

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5
gaccggtcga cccagatctg ggtcgacctg                                        30
```

UCP-2 PROMOTER AND USE THEREOF

CROSS-REFERENCES TO RELATED APPLICATIONS

The present invention is a 35 U.S.C. §371 national stage of PCT application PCT/JP99/07198, filed Dec. 22, 1999, which claims priority of Japanese Application Serial Number 366719/1998, filed Dec. 24, 1998.

FIELD OF THE INVENTION

This invention relates to a novel promoter for gene expression and its use. Specifically, this invention relates to a DNA containing the promoter region of human uncoupling protein-2 (UCP-2) gene, a transformant transformed with the said DNA, and a method for screening a compound or its salt that promotes or inhibits UCP-2 promoter activity.

BACKGROUND OF THE INVENTION

Uncoupling protein (UCP) is a proton transporter present in the mitochondrial inner membrane. Since UCP changes intracellular energy stored as fat to heat without using other energy consuming processes, UCP is considered to play an important role in maintenance of body temperature in homeothermal animals. Because of this function, UCP is considered to be an important factor that determines the efficiency of energy metabolism in homeothermal animals.

Three molecular species of uncoupling proteins have been identified to date, and are called uncoupling proteins-1 (UCP-1), -2 (UCP-2 or UCPH), and -3 (UCP-3).

UCP-1, the first isolated among the uncoupling protein family, is specifically expressed in brown fat cells (Line, C. S. and Klingerberg, M. (1980), FEBS Lett., 113, 299-303; Jacobsson, A. et al. (1985), J. Biol. Chem., 260, 16250-16254; Bouillaud, F. et al. (1986), J. Biol. Chem., 261, 1487-1490). UCP-2 was isolated as a homologue of UCP-1, and confirmed to be widely expressed in various organs (Gimeno, R. E. et al. (1997), Diabetes, Vol. 46, 900-906; Fleury, C., et al. (1997), Nature Genet., Vol. 15, 269-272). UPC-3 was isolated as a UCP specifically expressed in muscles (Vidal-Puig, A. et al. (1997), Biochem. Biophys. Res. Commun., Vol. 235, No. 1, 79-82; Boss, O. et al. (1997), FEBS Lett., 408, 33-38).

Generally, UCP-1 is considered to play an important role in maintenance of body temperature in rodents and hibernants. Basically, the number of brown fat cells that mainly express UCP-1 is lower in large sized animals and animal species inhabiting relatively warm climates (Rothwell, N. J. and Stock, M. J. (1979), Nature, Vol. 281, 31-35). Thus, in these animals including humans, UCP-2 or UCP-3, not UCP-1, may mainly be responsible for the control of the normal body temperature maintenance system and energy consuming process (Hosoda, K. et al. (1998), Obesity Research (Himan Kenkyu), Vol. 4, No. 3, 31-35; Enerback, S. et al. (1997), Nature, Vol. 387, 90-93).

Therefore, it may be possible to adjust the energy consumption/accumulation balance by controlling the gene expression or activity of UCP-2 or UCP-3 in these animals including humans (Hosoda, K. et al. (1998), Obesity Research (Himan Kenkyu), Vol. 4, No. 3, 31-35; Enerback, S. et al. (1997), Nature, Vol. 387, 90-93). In humans, enhancement of energy consumption is considered to promote consumption of not only dietary energy but also energy accumulated as fat. Accordingly, a decrease of body fat in humans may lead to improvement of obesity, the major cause of lifestyle diseases which become a problem in developed countries in recent years (Fleury, C. et al. (1997), Nature Genetics, Vol. 15, 269-272).

UCP-2 is also considered to be the major cause of fever observed in immunological inflammation such as infection, and inhibition of UCP-2 gene activity may reduce fever in immunological inflammation (Shigenaga, F. R. et al. (1998), Biochiem. Biophys. Res. Commun., Vol. 244, No. 1, 75-78).

In animals, especially in higher animals, organs differentiate and mature upon biogenesis, and develop to exert various functions. During this process, various organ-specific proteins are transiently or constantly expressed and provide the organ-specificity.

The general gene expression control system in animals includes the transcription induction system (promoter, enhancer). Promoter regions are generally located adjacent to the 5' upstream region of base sequences on chromosomes that are normally transcribed into messenger RNAs. Transcriptional regulatory protein is bound to or dissociated from a base sequence generally called the regulatory sequence in promoter regions, by which the transcription level of genes located downstream of the 3' region is regulated. Therefore, the transcriptional gene expression level can be estimated from the promoter activity to some extent. It is also known that the base sequences located downstream of the 3' region of a promoter do not affect the promoter activity in most cases. Therefore, promoter activity can be readily measured by substituting the transcribed messenger RNA for a base sequence encoding a protein with detectable enzyme activity (reporter). Recent technical innovation has made measurement of promoter activity using reporters very sensitive and simple, and measurement of promoter activity is used in drug screening and analysis of biological function.

For example, transcriptional regulatory factors of fat cell differentiation include peroxisome proliferation-activated receptor γ (PPAR γ) (Tontontz, P. et al. (1995), Curr. Opin. Genet. Dev., Vol. 5, 571-576), retinoid X receptor (RXR), CCAAT/enhancer binding protein (C/EBP) (Cornelius, P., et al. (1994), Annu. Rev. Nutr. Vol. 14, 99-129), etc. The transcriptional regulation by these factors is closely involved in the gene expression related to fat cells. It has been reported that the promoter regions of fat cell-related genes including UCP-2 gene contain the binding sequences for these transcriptional regulatory factors (regulatory sequences). These sequences in promoters are considered to play important roles in the actual regulation of UCP-2 transcription in vivo.

Accordingly, substances that enhance expression of UCP-2 or UCP-3 gene and protein may be used as anti-obesity drugs that reduce body fat content. UCP-2 is also considered to be the major cause of fever in immunological inflammation observed in infection, and substances that inhibit UCP-2 gene activity may reduce fever in immunological inflammation.

If a cell line expressing an appropriate reporter gene connected to the promoter region described above is established, the cell line may be used for screening a drug that promotes or inhibits the UCP-2 expression. In screening substances that may be used as anti-obesity drugs, responses more similar to those in vivo can be obtained by including these regulatory sequences in the promoter-reporter system, which is very advantageous in screening human anti-obesity drugs.

However, human UCP-2 promoter containing the regulatory sequence had not yet been identified, and no simple screening method using the promoter described above had been available for substances that affect the human UCP-2 gene expression.

DISCLOSURE OF THE INVENTION

The inventors performed extensive studies, and successfully obtained the human genomic UCP-2 gene using human UCP-2 cDNA fragments as probes in an attempt to establish a screening method for searching substances that affect the human UCP-2 gene expression. The gene was digested with restriction enzymes, and a 6.5 kb DNA of the upstream region containing a part of the structural gene encoding UCP-2 was obtained. From the DNA obtained, a 3.5 kb DNA containing the base sequence deduced to be the 1st and 2nd exons (2.5 kb DNA as the 5' upstream region) was re-cloned in plasmid DNA.

A plasmid DNA was constructed by splicing a luciferase gene as a reporter gene downstream of the 3.5 kb DNA. By measuring the luciferase activity in transformants of HepG2 cells and MG-63 cells differentiated to fat cell-like cells, UCP-2 promoter was found in the 3.3 kb DNA of the upstream region of the UCP-2 structural gene. As a result of detailed analysis, the regulatory sequence that may control the expression of UCP-2 was found.

The inventors proceeded with the study based on these findings, and obtained the present invention. The present invention relates to the following:

(1) A DNA containing uncoupling protein-2 (UCP-2) promoter region containing the regulatory sequence;

(2) A DNA described in (1) wherein the regulatory sequence is a sequence containing peroxisome proliferator response element (PPRE);

(3) A DNA described in (1) wherein the regulatory sequence is a sequence containing CCAAT/enhancer binding protein (C/EBP) binding sequence;

(4) A DNA described in (1) wherein the promoter region is a base sequence represented by position 1 to 2270 of SEQ ID NO: 1 or a base sequence containing a part of the said base sequence;

(5) A recombinant vector containing a DNA described in (1);

(6) A recombinant vector described in (5) containing a DNA having a structural gene under control of UCP-2 promoter region containing a regulatory sequence;

(7) A transformant transformed by a recombinant vector described in (5);

(8) A method for screening a compound or its salt that promotes or inhibits UCP-2 promoter activity characterized by use of a transformant described in (7);

(9) A method for screening a compound or its salt that promotes or inhibits heat production characterized by use of a transformant described in (7);

(10) A method for screening an anti-obesity drug, an antidiabetic drug, a depressor, an antihyperlipemic drug, and an antipyretic drug characterized by use of a transformant described in (7);

(11) A kit for screening a compound or its salt that promotes or inhibits UCP-2 promoter activity characterized by use of a transformant described in (7);

(12) A compound or its salt that promotes or inhibits UCP-2 promoter activity obtained using a screening method described in (8) or a screening kit described in (11);

(13) A compound or its salt that promotes or inhibits heat production obtained using a screening method described in (9); and

(14) A pharmaceutical composition containing a compound or its salt that promotes or inhibits UCP-2 promoter activity obtained using a screening method described in (8) or a screening kit described in (11).

BRIEF DESCRIPTION OF THE DRAWINGS

FIGS. 1A-1F show the base sequence of cDNA containing the human UCP-2 promoter region cloned in Example 1.

BEST MODE OF EMBODIMENT OF THE INVENTION

Figure 2:
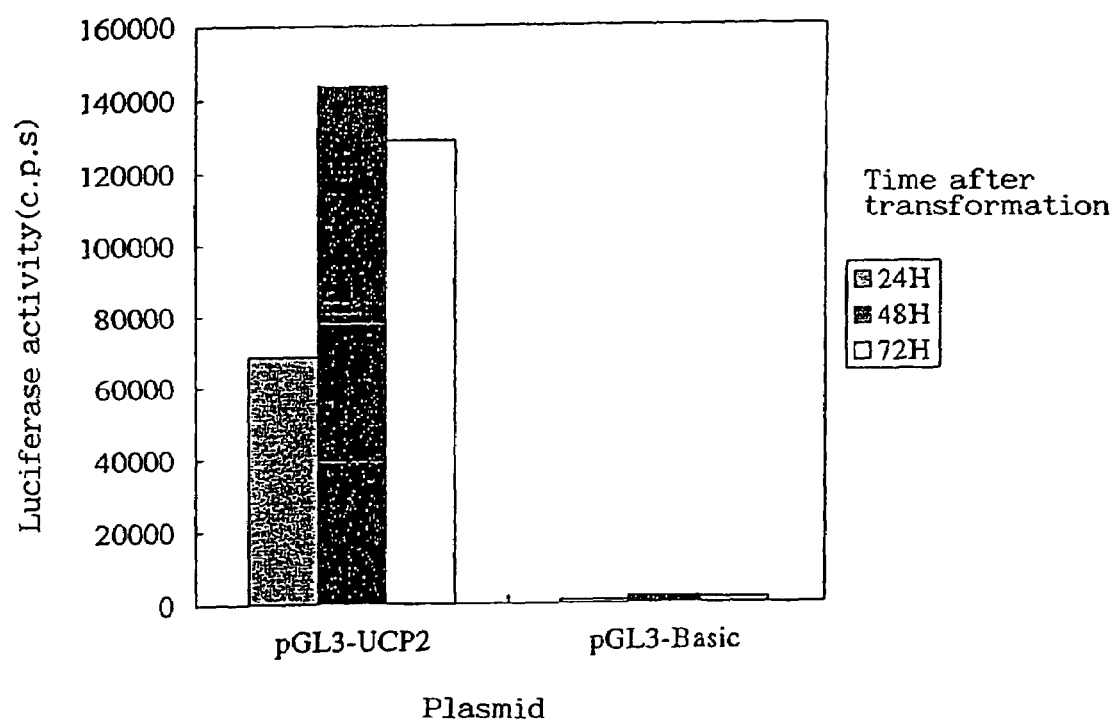
FIG. 2 shows the luciferase activity measured in Example 2.

A DNA containing the UCP-2 promoter region containing the regulatory sequence of this invention may be any DNA containing the regulatory sequence described below with UCP-2 promoter activity.

Specifically, a DNA of this invention may be any DNA containing the base sequence represented by position 1 to 2270 of SEQ ID NO: 1 or a part of said sequence.

A DNA of this invention may be genomic DNA, cDNA, and synthetic DNA derived from human and other mammalian cells (e.g. hepatocytes, splenocytes, neurocytes, glial cells, pancreatic β cells, bone marrow cells, mesangium cells, Langerhans' cells, epidermal cells, epithelial cells, endothelial cells, fibroblasts, fiber cells, muscle cells, fat cells, immune cells (e.g. macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells, and interstitial cells, or precursor cells, stem cells, or cancer cells of said cells, and any tissue in which said cells are present, for example, the brain, each region of the brain (e.g. olfactory bulbs, amygdalloidal nucleus, basal ganglia, hippocampus, thalamus, hypothalamus, cerebral cortex, medulla oblongata, cerebellum), spinal cord, pituitary gland, stomach, pancreas, kidneys, liver, gonads, thyroid gland, gallbladder, bone marrow, adrenal glands, skin, muscle, lung, digestive tract (e.g. large intestine, small intestine), blood vessels, heart, thymus, spleen, salivary glands, peripheral blood, prostate, testes, ovaries, placenta, uterus, bones, cartilages, joints, and skeletal muscles.

Specifically, a recombinant DNA containing the human UCP-2 promoter region of this invention can be obtained as follows.

Using the base sequence corresponding to the previously reported amino acid sequences of human UCP cDNA (Fleury, C. et al. (1997), Nature Genet. Vol. 15, 269-272) as the probes, for example, human genomic library inserted in EMBL3 vector is screened by a publicly known method, and λ phage clones to which the probes hybridize are obtained. A DNA is extracted from these phage clones, and the restriction enzyme map of the human gene inserted in the clones is prepared.

DNA fragments are prepared by digestion with restriction enzymes, and the fragments hybridizing to the probes for the most upstream region of the cDNA are re-cloned in vectors for animal cells such as pCD vector, cDM8 vector (Aruffo, A. and Seed, B. (1987), Proc. Natl. Acad. Sci. USA, 84, 8573-8577), and retrovirus vector (Cone, R. D. and Mulligan, R. C. (1984), Proc. Natl. Acd. Sci. USA, 81, 6349-6353), and *Escherichia coli* plasmids such as pUC vector (Vieira, J. and Messing, J. (1987), Methods in Enzymology, 153, 3-11), and pCR-blunt vector (Ausubel, F. M. et al. (1994), Current Protocols in Molecular Biology), but not limited to these vectors. The base sequences of the cloned DNAs are determined, and the position of the translation initiation codon on the gene can be determined by, for example, comparing the base sequence with the cDNA sequence. The position of the transcriptional initiation site on the gene can also be determined by comparing the base sequence with the 5' end of known cDNA. By investigating motifs throughout the entire sequence, the binding site of known transcriptional regulatory factors can be determined.

The isolated DNA can be used without modification or if necessary, after digestion with restriction enzymes or being bound by linkers.

To measure the promoter activity, a detectable structural gene may be spliced downstream of the promoter region. For the structural gene spliced downstream of the promoter region, various reporter genes are used. For the reporter gene, luciferase gene, chloramphenicol acetyltransferase (CAT) gene, alkaline phosphatase gene, and β-galctosidase gene are commonly used, but any other structural genes for which a method of detecting the gene product is available may be used. To insert the above structural gene into the vector, the structural gene is ligated to an appropriate restriction enzyme site located downstream of the promoter region in the correct transcriptional orientation.

For the host transformed by the recombinant vector described above, for example, *Escherichia* genus, *Bacillus* genus, yeast, insect cells, insects, and animal cells are used.

Specific examples of the host *Escherichia* genus are *Escherichia coli* K12.DH1 [Proceedings of the National Academy of Sciences of the USA (Proc. Natl. Acad. Sci. USA), Vol. 60, 160 (1968)], JM103 [Nucleic Acids Research, Vol. 9, 309 (1981)], JM109, JA221 [Journal of Molecular Biology, Vol. 120, 517 (1978)], HB101 [Journal of Molecular Biology, Vol. 41, 459 (1969)], and C600 [Genetics, Vol. 39, 440 (1954)].

For the host *Bacillus* genus, for example, *Bacillus subtilis* MI114 [Gene, Vol. 24, 255 (1983)] and 207-21 [Journal of Biochemistry, Vol. 95, 87 (1984)] are used.

For the host yeast, for example, *Saccharomyces cerevisiae* AH22, AH22R⁻, NA87-11A, DKD-5D, 20B-12, *Schizosaccharomyces pombe* NCYC1913, NCYC2036, and *Pichia pastoris* are used.

For the host insect cells, for example, when the virus is AcNPV, *Spodoptera frugiperda* cells (Sf cells), MG1 cells derived from the middle gut of *Trichoplusia ni*, High Five™ cells derived from *Trichoplusia ni* eggs, *Mamestra brassicae*-derived cells, and *Estigmena acrea*-derived cells are used. When the virus is BmNPV, silkworm-derived cell line *Bombyx mori* N (BmN cells) are used. For said Sf cells, for example, Sf9 cells (ATCC CRL1711), Sf21 cells (Vaughn, J. L. et al., In Vivo, 13, 213-217 (1977)) are used.

For the host insect, for example, silkworm larvae are used [Maeda et al., Nature, Vol. 315, 592 (1985)].

For the host animal cells, for example, monkey COS-7 cells, Vero, Chinese hamster CHO cells (CHO), dhfr gene-deficient Chinese hamster cells CHO (CHO (dlfr⁻) cells), mouse L cells, mouse AtT-20, mouse myeloma cells, rat GH3, mouse fibloblast 3T3-L1, human liver cancer cell HepG2 (HepG2 cells), human sarcoma cell MG-63 (MG-63 cells), human FL cells, white fat cells, egg cells, ES cells (Evans, M. J. and Kaufman, K. H. (1981), Nature, 292, 154), and differentiation-induced cells under appropriate differentiation conditions are used.

Animal cells, especially white fat cells, may be used. As a process of DNA transfer to individual animals, egg cells and ES cells (Evans, M. J. and Kaufman, K. H. (1981), Nature, 292, 154) are used.

For the method of transforming these cells, the calcium phosphate method (Graham et al. (1973), Virology, 52, 456), electroporation (Ishizaki et al. (1986), Cell Engineering (Saibo Kogaku), 5, 577), and microinjection are used.

More specifically, for transformation of bacteria of *Escherichia* genus, for example, the methods published in Proc. Natl. Acad. USA, Vol. 69, 2110 (1972) and Gene, Vol. 17, 107 (1982) are used.

Bacteria of *Bacillus* genus can be transformed following, for example, the method published in Molecular & General Genetics, Vol. 168, 111 (1979).

Yeast can be transformed following, for example, the methods published in Methods in Enzymology, Vol. 194, 182-187 (1991) and Proc. Natl. Acad. USA, Vol. 75, 1929 (1978).

Insect cells and insects can be transformed following, for example, the method published in Bio/Technology, 6, 47-55 (1988).

Animal cells can be transformed by, for example, the methods described in Cell Engineering (Saibo Kogaku), Separate Vol. 8, New Cell Engineering Experimental Protocol, 263-267 (1995) (Shujun-sha) and Virology, Vol. 52, 456 (1973).

The transformant described above is cultured in the presence of the specified compound, and by measuring and comparing the gene product in the cultured material, the ability of controlling the promoter activity of the compound can be examined.

The transformant is cultured by publicly known methods. For the medium for culturing the transformant using *Escherichia* and *Bacillus* hosts, liquid medium is appropriate, such as that which contains carbon source, nitrogen source, inorganic compounds, and other substances necessary for the growth of the transformants. The carbon source includes, for example, glucose, dextrin, soluble starch, and sucrose, etc. The nitrogen source includes, for example, inorganic and organic compounds such as ammonium salts, nitrates, cornsteep liquor, peptone, casein, meat extract, soybean cake, and potato extract, etc. The inorganic compounds include, for example, calcium chloride, sodium dihydrogen phosphate, and magnesium chloride, etc. Yeast extract, vitamins, and growth-stimulating factors may be added. The pH about 5-8 is desirable for the culture medium.

For the culture medium for bacteria of *Escherichia* genus, for example, M9 medium containing glucose and casamino acid (Miller, Journal of Experiments in Molecular Genetics, 431-433, Cold Spring Harbor Laboratory, New York, 1972) is preferred. When a higher efficiency of the promoter is required, reagents such as 3-β-indolylacrylic acid may be added. When the host is bacteria of *Escherichia* genus, the bacteria are generally cultured at about 15-43° C. for about 3-24 hours, and the culture may be aerated or stirred if necessary.

When the host is bacteria of *Bacillus* genus, the bacteria are generally cultured at about 30-40° C. for about 6-24 hours, and the culture may be aerated or stirred if necessary.

For the medium for culturing the transformant in yeast host, for example, Burkholder minimum medium [Bostian, K. L. et al., Proc. Natl. Acad. Sci. USA, Vol. 77, 4505 (1980)] and SD medium containing 0.5% casamino acid [Bitter, G. A. et al., Proc. Natl. Acd. Sci. USA, Vol. 81, 5330 (1984)] are used. The pH of the medium is preferably adjusted to about 5-8. The culture conditions are generally about 20-35° C. for about 24-72 hours, and the culture may be aerated or stirred if necessary.

For the medium for culture of the transformants in insect cells and insect hosts, Grace's insect medium [Grace, T. C. C., Nature, 195, 788 (1962)] containing appropriate supplements, such as inactivated 10% bovine serum, is used. The pH of the medium is preferably adjusted to about 6.2-6.4. Usually, the culture conditions are at about 27° C. for about 3-5 days, and the culture may be aerated or stirred if necessary.

For the culture medium of the transformants in animal cell hosts, for example, MEM containing about 5-20% fetal calf serum [Science, Vol. 122, 501 (1952)], DMEM [Virology, Vol. 8, 396 (1959)], RPMI 1640 medium [The Journal of the American Medical Association, Vol. 199, 519 (1967)], and 199 medium [Proceeding of the Society for the Biological Medicine, Vol. 73, 1 (1950)] are used. The pH is preferably adjusted to about 6-8. Usually, the culture conditions are about 30-40° C. for about 15-60 hours, and the culture may be aerated or stirred if necessary.

Specifically, the regulatory sequence may be any sequence of the base sequence represented by position from 1 to 2270 of SEQ ID NO: 1 to which the UCP-2 transcriptional regulatory factor can bind, such as sequences containing peroxisome proliferator response element (PPRE) represented by position 284 to 296 of SEQ ID NO: 1, sequences containing CCAAT/enhancer binding protein (C/EBP) binding sequence represented by position 1316 to 1320, 1364 to 1368, or 1698 to 1692 of SEQ ID NO: 1, sequences containing glucocorticoid response element (GRE) represented by position 753 to 758, 1023 to 1030, or 1450 to 1455 of SEQ ID NO: 1, and sequences containing MyoD represented by position 1428 to 1437 of SEQ ID NO: 1.

Therefore, a DNA of this invention contains the promoter region containing the said regulatory sequence, and a DNA of this invention may contain multiple numbers of the said regulator sequences.

For the base sequences containing a part of the base sequence represented by position 1 to 2270 of SEQ ID NO: 1, any base sequences containing the regulatory sequence described above may be used. Specifically, the base sequence represented by position 255 to 430 of SEQ ID NO: 1, the base sequence represented by position 255 to 717 of SEQ ID NO: 1, the base sequence represented by position 717 to 1133 of SEQ ID NO: 1, the base sequence represented by position 1133 to 1389 of SEQ ID NO: 1, and the base sequence represented by position 255 to 1857 of SEQ ID NO: 1 are used.

Furthermore, the base sequence represented by position 571 to 2270 of SEQ ID NO: 1, the base sequence represented by position 717 to 2270 of SEQ ID NO: 1, the base sequence represented by position 1133 to 2270 of SEQ ID NO: 1, the base sequence represented by position 1389 to 2270 of SEQ ID NO: 1, and the base sequence represented by position 1634 to 2270 of SEQ ID NO: 1 are used.

Since a DNA of this invention contains the UCP-2 promoter region containing the regulatory sequence, using the transformant described above, a compound or its salt that promotes or inhibits UCP-2 promoter activity (e.g. a compound that promotes or inhibits heat production) can be screened. The said screening method, screening kit, and the said compound or its salt that promotes or inhibits UCP-2 promoter activity obtained using the said screening method and screening kit are specifically explained below.

(1) A method for screening a compound or its salt that promotes or inhibits UCP-2 promoter activity (e.g. a compound that promotes or inhibits heat production)

A transformant transformed by the DNA of this invention described above is useful for searching for and identifying a compound or its salt that promotes or inhibits UCP-2 promoter activity of this invention.

A method for identifying a compound or its salt that promotes or inhibits UCP-2 promoter activity of this invention is characterized by measuring and comparing polypeptide expression between a transformant of this invention contacting a test compound and the transformant lacking the UCP-2 promoter region of this invention contacting the test compound.

The said test compound includes peptides, proteins, non-peptide compounds, synthetic compounds, and fermentation products, etc., and these test compounds may be novel compounds or known compounds.

For the polypeptide to be expressed, polypeptides encoded by the structural genes described above (preferably reporter genes) are used.

For the quantification method of polypeptide expression, for example, quantification of luciferase activity according to the method described by Brasier, A. R. et al. (1989) in Biotechniques Vol. 7, 1116-1122, is used.

(2) A kit for screening a compound or its salt that promotes or inhibits UCP-2 promoter activity (e.g., a compound that promotes or inhibits heat production)

A kit for identifying a compound or its salt that promotes or inhibits UCP-2 promoter activity (e.g., a compound that promotes or inhibits heat production) is characterized by use of the transformant described above. Examples of the kit for identifying a compound or its salt that promotes or inhibits UCP-2 promoter activity of this invention are as follows.

① Screening Reagents

1. Cell Culture Medium

Dulbecco's modified Eagle's medium (Gibco Co.) supplemented with 10% fetal calf serum (Gibco Co.)

2. Cell Differentiation Medium

Dulbecco's modified Eagle's medium (Gibco Co.) supplemented with 5% rabbit serum (Gibco Co.)

3. Plasmid for Measurement of UCP-2 Promoter Activity pGL3-basic (Promega Co.) plasmid DNA carrying UCP-2 promoter sequence of this invention and a structural gene (e.g. luciferase gene) inserted downstream of the UCP-2 promoter 4. Host Cell Line MG-63 cells (osteosarcoma cell line, obtained from ATCC)

5. Test Compounds

Aqueous solutions are stored at 4° C. or −20° C., and diluted to 1 μM with cell differentiation medium at the time of use. Test compounds that are slightly soluble in water are dissolved in dimethylforamide, DMSO, and methanol.

② Screening Method

Host cells are seeded in 96-well microplates at a density of $1 \times 10^5$ cells/well, and cultured in an incubator at 37° C. in 5% $CO_2$ overnight.

The cells are transfected with 1 μg/well of plasmid for UCP-2 promoter activity measurement.

One hour after transfection, 0.1 ml of test compound is added to each well, and the cells are cultured in an incubator at 37° C. in 5% $CO_2$ for 48 hours.

After culture, 0.1 ml of PicaGene LT (Toyo Ink Co.) is added to each well, stirred for five minutes, and then the luminescence is measured using a 96-plate measurement system (Amersham-Pharmacia Co.).

(3) A compound or its salt that promotes or inhibits UCP-2 promoter activity (e.g. a compound that promotes or inhibits heat production) obtained using the screening method described in (1) and the screening kit described in (2)

If a compound that promotes or inhibits UCP-2 promoter activity is found using the screening method described in (1) or the screening kit described in (2), the compound may be used as a prophylactic or therapeutic drug for obesity syndrome because the compound increases or promotes heat production, and thus, the compound may be used as a radical therapeutic drug for lifestyle diseases (diabetes, hypertension, hyperlipidemia). Therefore, the compound may be used as an anti-obesity drug, an antidiabetic drug, a depressor, and an antihyperlipemic drug.

When the compound reduces or inhibits the promoter activity, the compound may be used as an antipyretic drug because the compound decreases or inhibits heat production.

A salt of the compound obtained using the screening method or the screening kit described above includes a pharmaceutically acceptable salt. For example, salts formed with inorganic bases, organic bases, inorganic acids, organic acids, and basic and acidic amino acids are used.

Preferred salts formed with inorganic bases include alkaline metal salts such as sodium salts and potassium salts, alkaline earth metal salts such as calcium salts and magnesium salts, and aluminum salts and ammonium salts, etc.

Preferred salts formed with organic bases include salts formed with trimethylamine, triethylamine, pyridine, picoline, 2,6-lutidine, ethanolamine, diethanolamine, triethanolamine, cyclohexylamine, dicyclohexylamine, and N,N'-dibenzylethylenediamine, etc.

Preferred salts formed with inorganic acids include salts formed with hydrochloric acid, hydrobromic acid, sulfuric acid, and phosphoric acid, etc.

Preferred salts formed with organic acids include salts formed with formic acid, acetic acid, propionic acid, fumaric acid, oxalic acid, tartaric acid, maleic acid, citric acid, succinic acid, malic acid, methanesulfonic acid, benzenesulfonic acid, and benzoic acid, etc.

Preferred salts formed with basic amino acids include salts formed with arginine, lysine, and ornithine, etc., and preferred salts formed with acidic amino acids include salts formed with aspartic acid and glutamic acid, etc.

When the said compound or its salt is used as a prophylactic and/or therapeutic drug for the diseases described above, the preparation can be provided by conventional methods.

For example, the said compound or its salt can be orally administered as sugar coated tablet, capsule, elixir, and microcapsule, etc., or non-orally as injection such as aseptic solution in water or other pharmaceutically acceptable liquid and suspension. Preparations can be manufactured by, for example, mixing with physiologically acceptable known carrier, flavor, filler, vehicle, antiseptic, stabilizer, and binder in a unit-dosage form required for generally approved drug preparation. The amount of the active ingredient is set for preparation of an appropriate dosage within the specified range.

For the additive miscible with tablets and capsules, for example, binders such as gelatin, cornstarch, tragacanth and acacia, fillers such as crystalline cellulose, swellings such as cornstarch, gelatin, and alginic acid, lubricants such as magnesium stearate, sweeteners such as sucrose, lactose and saccharin, and flavors such as peppermint, akamono oil and cherry are used. When the unit-dosage form is a capsule, a liquid carrier such as fat or oil may be included. Aseptic compositions for injection can be formulated following the usual preparation procedure, such as dissolving or suspending the active substance in vehicle, e.g., water for injection, and natural plant oils, e.g., sesame oil and coconut oil. For an aqueous solution for injection, for example, physiological saline and isotonic solutions (e.g., D-sorbitol, D-mannitol, sodium hydrochloride) containing glucose and other adjuvant(s) are used. Appropriate dissolution-assisting agents, for example, alcohol (e.g., ethanol), polyalcohol (e.g., propylene glycol, polyethylene glycol), and nonionic surfactant (e.g., polysorbate 80(TM), HCO-50) may be combined. For an oil-based solution, for example, sesame oil and soybean oil are used, and dissolution-assisting agents such as benzyl benzoate and benzyl alcohol may be combined.

The prophylactic/therapeutic drugs described above may be combined with, for example, buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzylalcohol, phenol), and antioxidants. The preparation for injection is usually filled in appropriate ampoules.

The preparations obtained as described above are safe and low toxic, and can be administered to, for example, humans and mammals (e.g., rats, mice, rabbits, sheep, pigs, cattle, cats, dogs, monkeys, etc.).

The dosage of the said compound or its salt differs depending on the target individual, target organ, symptoms, and administration method, etc. When it is administered orally, in general, for adults (60 kg body weight), about 0.1-100 mg per day, preferably about 1.0-50 mg per day, more preferably about 1.0-20 mg per day is administered. When it is administered non-orally, the dosage per dosing differs depending on the target individual, target organ, symptoms, and administration method, etc. For example, in case of injection in general, for adults (60 kg body weight), it is desirable to intravenously inject about 0.01-30 mg per day, preferably about 0.1-20 mg per day, more preferably about 0.1-10 mg per day. Converting the dosage for 60 kg, the said compound or its salt can be administered to other animals.

In this specification and drawings, the codes of bases and amino acids are according to IUPAC-IUB Commission on Biochemical Nomenclature or common codes in the art. The examples are shown below. For amino acids that may have an optical isomer, the L form is presented unless specified otherwise.

DNA: deoxyribonucleic acid
cDNA: complementary deoxyribonucleic acid
A: adenine
T: thymine
G: guanine
C: cytosine The SEQ ID NOs shown in the Sequence Listing of this Specification present the sequences below.

[SEQ ID NO: 1] Base sequence of cDNA containing human UCP-2 promoter region cloned in Example 1.

[SEQ ID NO: 2] Synthetic DNA used in screening of cDNA containing human UCP-2 promoter region.

[SEQ ID NO: 3] Synthetic DNA used in screening of cDNA containing human UCP-2 promoter region.

[SEQ ID NO: 4] Synthetic DNA used in screening of cDNA containing human UCP-2 promoter region.

[SEQ ID NO: 5] Synthetic DNA used in screening of cDNA containing human UCP-2 promoter region.

EXAMPLES

The present invention is explained in detail below showing examples, but it is not intended to limit the scope of this invention to the description.

*Escherichia coli* transformant TOP10/pCR-ucp2p5'#1-10 obtained in the Example 1 described below was deposited with the Ministry of International Trade and Industry, Agency of Industrial Science and Technology, National Institute of Bioscience and Human Technology (NIBH) as deposit number FERM BP-6587 on Nov. 24, 1998 and with Institute for Fermentation, Osaka (IFO) as deposit number IFO 16219 on Nov. 11, 1998.

Example 1

Cloning of Human UCP-2 cDNA

Using 0.5 ng of human kidney cDNA (Clontech Laboratory, California, USA) as the template and the base sequence of base number 55 to 82: 5'-ATGGTTGGGTTCAAGGCCA-CAGATGTGCCC-3' (SEQ ID NO: 2) of previously reported human UCP-2 cDNA [Gimeno, R. et al. (1997), Diabetes, Vol. 46, 900-906] and the base sequence complementary to base number 1300 to 1329: 5'-ATACAGGCCGATGCGGA-CAGAGGCAAAGCT-3' (SEQ ID NO: 3) as oligonucleotide primers, human UCP-2 gene was amplified by PCR (after heating at 94° C. for 5 min., a cycle consisting of heating at 94° C. for 1 min, 55° C. for 0.5 min and 72° C. for 1.5 min was repeated 30 times, followed by heating at 72° C. for 5 min), then inserted into pCR-blunt vector. Using this plasmid DNA carrying the insert as the template, oligonucleotide primers were prepared, and probes were prepared using PCR DIG probe synthesis kit (Boehringer-Mannheim Co.) following the enclosed instructions. Using the prepared probes, a human genomic DNA library (Clontech Laboratory, California, USA) in 3×10$^6$ phage was screened using nitrocellulose filters. Plaque hybridization was performed using DIG Easy hyb (Boehringer-Mannheim Co.), DIG Wash and Block Buffer Set (Boehringer-Mannheim Co.), and DIG nucleic acid detection kit (Boehringer-Mannheim Co.) following the enclosed instructions. As a result, eight positive clones were obtained from 3×10$^6$ phage. Of these clones, an inner primer of non-coding exon of previously reported human UCP-2 cDNA sequence [Gimeno, R. E. et al. (1998), Diabetes, 47 (4), 685-687] was synthesized (5'-CAAAGCTGCCAGTG-GCTATCATGGCCCG-3') (SEQ ID NO: 4), and a clone containing the non-coding exon was detected by PCR using a primer containing EMBL3 sequence (5'-GACCGGTCGAC-CCAGATCTGGGTCGACCTG-3') (SEQ ID NO: 5), and a genomic clone containing the 5' upstream region of UCP-2 was obtained. From the genomic clone, a 3.5 kbp fragment containing UCP-2 promoter region was prepared and inserted into pCR-blunt vector (Invitrogen Co.), and transformant *E. coli* TOP/10 pCR-UCP2P5' #1-10 was prepared. After that, the restriction enzyme map was prepared, and the base sequence was determined. The determined base sequence (SEQ ID NO: 1) is shown in FIGS. 1A-1F. As shown in FIGS. 1A-1F, base number 2271-2326 and 3416-3505 were completely consistent with human UCP-2 cDNA (Gimeno, R. E. et al. (1998), Diabetes, 47 (4), 685-687). Furthermore, the terminal base sequences of the conserved regions were consistent with the Shahnborn rule, which is the characteristic of intron-exon boundary base sequence, suggesting that the conserved base sequences are introns. A sequence likely to be a CpG island (base number about 2070-2270), which is a characteristic of promoters not containing a TATA-box sequence, was also confirmed upstream of the first exon. In the promoter sequence described above, PPRE (base number 284-296), which is the regulatory sequence of promoters of fat cell-related genes, and three C/EBP binding sites (base number 1316-1320, 1364-1368, 1698-1692) were confirmed.

Example 2

Examination of Human UCP-2 Gene Promoter Activity

To confirm the promoter activity of the cloned genomic DNA fragment, a luciferase assay was performed. pGL3-Basic plasmid (Promega Co.) carrying firefly luciferase gene as the reporter gene was used for the vector. As the internal standard, pRL-SV40 plasmid (Promega Co.) expressing sea pansy luciferase under control of SV40 promoter was used.

An EcoRI fragment (3.5 kbp) was isolated from the genomic human UCP-2 DNA and blunted using Blunting High Kit (TOYOBO Co.), and then ligated to SmaI-digested pGL3-Basic plasmid DNA. Following the above procedure, a human UCP-2 promoter/luciferase vector (pGL3-UCP2) was constructed in which the base number 1-3505 shown in FIGS. 1A-1F was inserted into pGL3-Basic vector. The constructed human UCP-2 promoter/luciferase vector was transiently transfected in HepG2 cells, in which constant expression of UCP-2 was confirmed by RT-PCR, and the activity was examined.

HepG2 cells were seeded in 24-well multiplates (Nunk Co.) at a density of 60,000 cells/well, and cultured at 37° C. in 5% $CO_2$ overnight. Using SuperFect Transfection Reagent (QIAGEN Co.), cells were transiently transfected with 1 μg of human UCP-2 promoter/luciferase vector DNA or pGL3-Basic DNA and 0.1 μg of pRL-SV40 DNA. The procedure was performed according to the enclosed instructions. Then, the cells were cultured at 37° C. in 5% $CO_2$ for 24 hours, and the luciferase activity was detected using PicaGene Dual Sea Pansy (Nippon Gene Co.) according to the enclosed instructions. The measurement data were presented as relative activity to the internal standard value of pRL-SV40-derived sea pansy luciferase activity. The results are shown in FIG. 2. The human UCP-2 promoter/luciferase vector-derived luciferase activity was markedly higher than that of pGL3-Basic lacking the promoter. Therefore, the genomic DNA of human UCP-2 gene of this invention has a promoter activity reflecting the in vivo UCP-2 gene expression system.

Example 3

Examination of Human UCP-2 Gene Promoter Activity in Human Differentiated Fat Cell-Like Cells Using the human UCP-2 promoter/luciferase vector DNA obtained in Example 2, the promoter activity in human fat cell-like cells differentiated from MG-63 cells was confirmed.

MG-63 cells were seeded in 24-well multiplates (Nunk Co.) at a density of 100,000 cells/well, and cultured at 37° C. in 5% $CO_2$ overnight. Using SuperFect Transfection Reagent (QIAGEN Co.), cells were transiently transfected with 1 μg of human UCP-2 promoter/luciferase vector DNA or pGL3-

Figure 3:
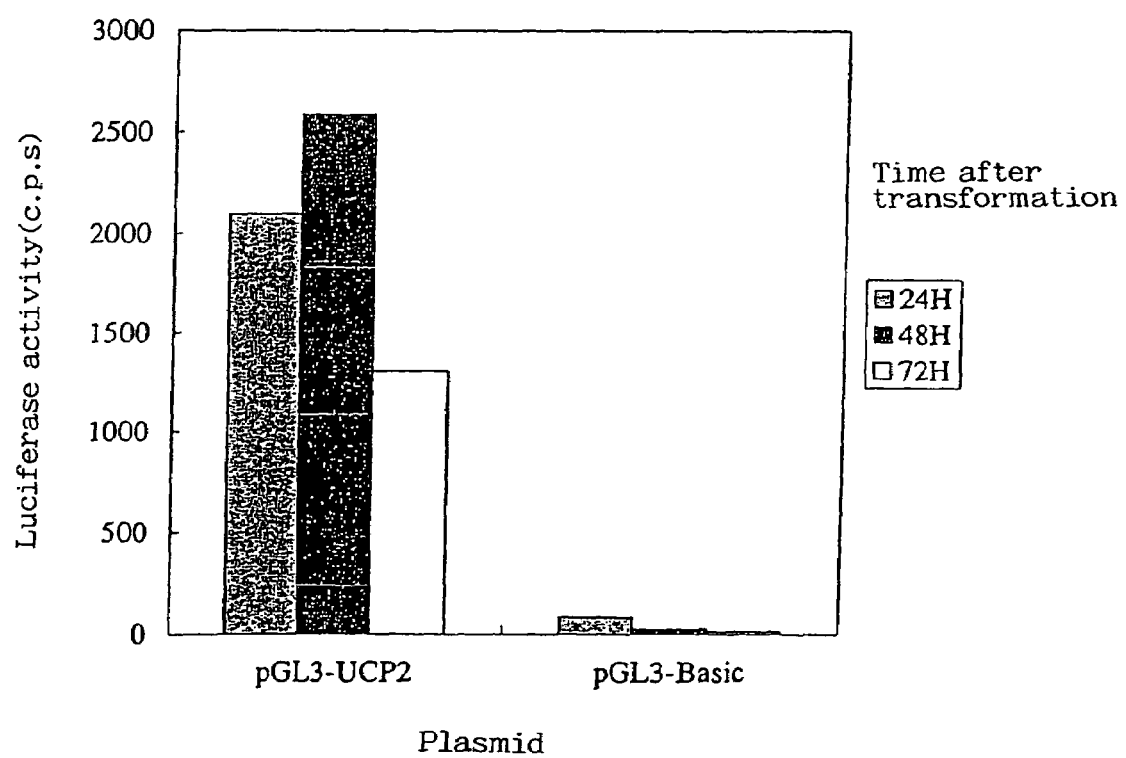
FIG. 3 shows the luciferase activity measured in Example 3.

Basic DNA and 0.1 µg of pRL-SV40 DNA. The procedure was performed according to the enclosed instructions. The culture medium was replaced with Dulbecco's modified Eagle's medium (DMEM) (Gibco Co.) containing 5% rabbit serum (Gibco Co.), and differentiation to fat cell-like cells was induced. Then, the cells were cultured at 37° C. in 5% $CO_2$ for 24, 36, and 72 hours. After culturing, the luciferase activity was detected in each culture as described in Example 2. The measurement data were presented as relative activity to the internal standard value of pRL-SV4-derived sea pansy luciferase activity. The results are shown in FIG. 3. The human UCP-2 promoter/luciferase vector-derived luciferase activity was markedly higher than that of pGL3-Basic lacking the promoter in fat cell-like cells differentiated from human MG-63 cells. Therefore, the genomic DNA of human UCP-2 gene of this invention has the promoter activity reflecting the in vivo UCP-2 gene expression system in fat cell-like cells differentiated from human MG-63 cells.

Example 4

Preparation of Human UCP-2 Promoter-Deficient Vector

Figure 4:
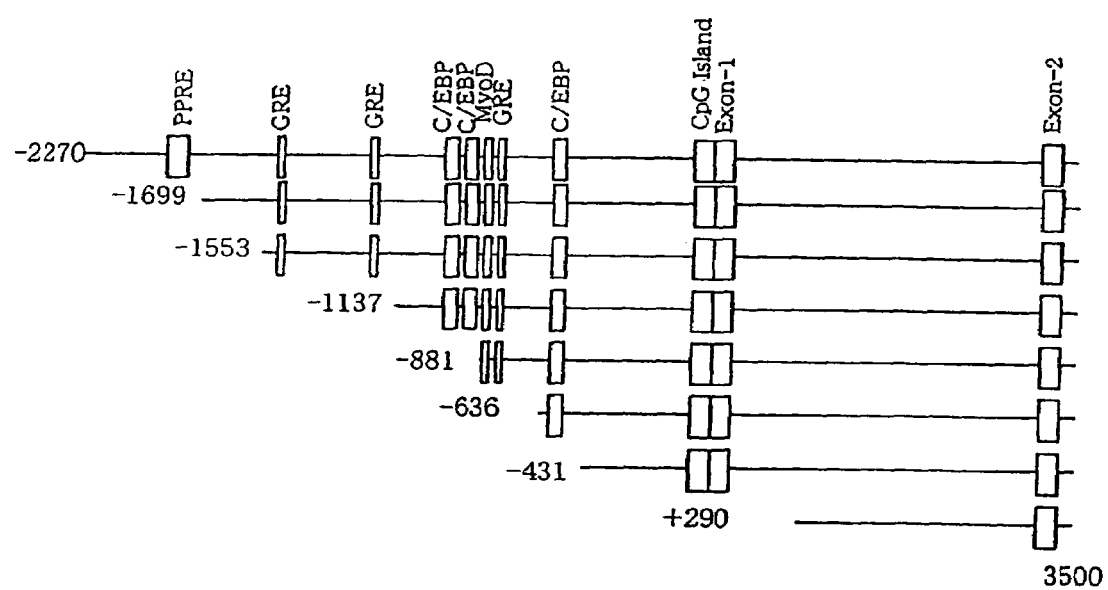
FIG. 4 shows the structure of the UCP-2 promoter deficient-clones constructed in Example 4. The numbers in the Figure represent the base number starting from the transcription initiation site.

The human UCP-2 promoter/luciferase vector prepared in Example 2 was digested with KpnI and MluI, and the human UCP-2 promoter-deficient vector shown in FIG. 4 was prepared using the Deletion Kit for Kilo-Sequence (Takara Shuzo Co.) by following the protocol. The plasmid digested with KpnI and MluI was purified by phenol extraction and ethanol precipitation. Then, the precipitated DNA was treated with exonuclease III and sampled every one minute, and the reaction was terminated. The samples were treated with Mung bean nuclease and the ends were blunted. The ends were restored by Klenow fragment, and the DNA was circularized by DNA ligase. The circularized DNAs were re-treated with MluI to linearize plasmids in which deletion did not occur. E. coli JM 109 competent cells (Takara Shuzo Co.) were transformed with this reaction solution. The deficient clone plasmids thus obtained were purified by publicly known methods. The molecular weights of the deficient plasmids were confirmed by agarose gel electrophoresis, and clones were selected. The base sequences of these clones were confirmed by publicly known method.

Figure 5:
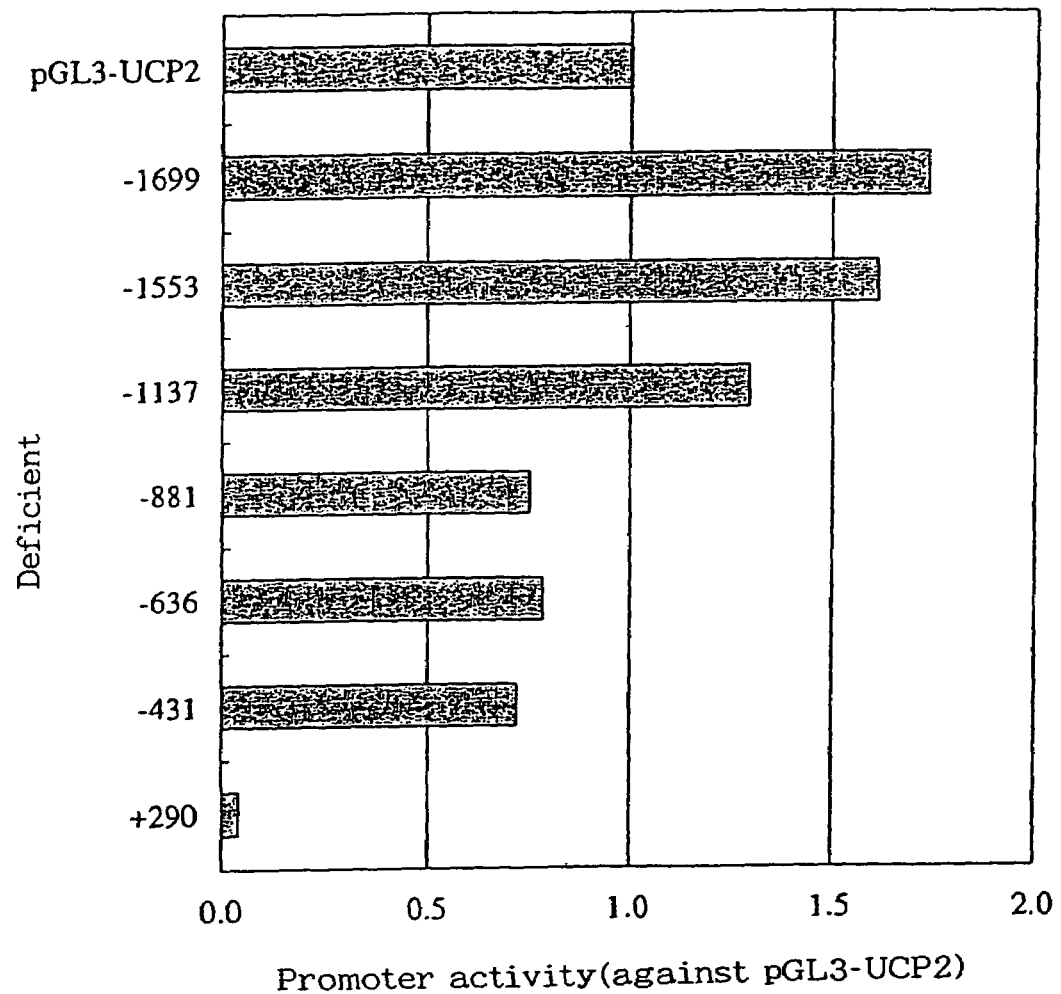
FIG. 5 shows the promoter activity measured in Example 4.

Using these plasmids, the promoter activity was measured by the procedure described in Example 2 (FIG. 5).

When the base sequence containing PPRE (base number 284-296) shown in Example 1 was deleted, about 70% increase in the UCP-2 promoter activity was observed, suggesting that this sequence region has a UCP-2 promoter suppressor activity. When the base sequence containing the two C/EBP binding sites (base number 1316-1320 and 1364-1368) was deleted, about 30% of the UCP-2 promoter activity decreased, suggesting that the base sequence containing these two C/EBP binding sites has a UCP-2 promoter enhancer activity. When 290 bases were deleted from the transcriptional initiation site toward downstream, no UCP-2 promoter activity was detected. Therefore, the genomic DNA of human UCP-2 gene of this invention has a promoter activity reflecting the in vivo UCP-2 gene expression control system.

INDUSTRIAL APPLICABILITY

Since UCP-2 promoter of this invention contains the regulatory sequence, it has higher activity reflecting the in vivo UCP-2 DNA expression system in humans than the promoter lacking the regulatory sequence. Therefore, the UCP-2 promoter of this invention can be used as a promoter inserted in vectors for treatment of human diseases and providing drug-screening systems under conditions closer to the in vivo environment in humans.

---

The invention claimed is:

1. A method for screening for a compound or its salt that promotes or inhibits a human UCP-2 promoter activity, which comprises:

a. measuring the expression level of a reporter molecule in a transformant, with a DNA consisting of a human UCP-2 promoter sequence and a base sequence encoding the reporter molecule inserted downstream of the human UCP-2 promoter, contacted to a first sample of the compound or its salt and that in a control transformant, with a DNA consisting of a base sequence encoding the reporter molecule but with no DNA consisting of human UCP-2 promoter, contacted to a second sample of the compound or its salt, wherein the human UCP-2 promoter sequence consists of (1) a base sequence consisting of nucleotides 1 to 2270 of SEQ ID NO: 1, or (2) a base sequence selected from the group consisting of nucleotides 255 to 430 of SEQ ID NO: 1, nucleotides 255 to 717 of SEQ ID NO: 1, nucleotides 717 to 1133 of SEQ ID NO: 1, nucleotides 1133 to 1389 of SEQ ID NO: 1, nucleotides 255 to 1857 of SEQ ID NO: 1, nucleotides 571 to 2270 of SEQ ID NO: 1, nucleotides 717 to 2270 of SEQ ID NO: 1, nucleotides 1133 to 2270 of SEQ ID NO: 1, nucleotides 1389 to 2270 of SEQ ID NO: 1, and nucleotides 1634 to 2270 of SEQ ID NO: 1; and b. comparing the expression levels thereof.

2. A kit for screening for a compound or its salt that promotes or inhibits a human UCP-2 promoter activity, which comprises:

a. a medium for culturing a host animal cell line;

b. a plasmid for measurement of the human UCP-2 promoter activity, which comprises:

i. plasmid DNA carrying a DNA consisting of a human UCP-2 promoter sequence, wherein the human UCP-2 promoter sequence consists of (1) a base sequence consisting of nucleotides 1 to 2270 of SEQ ID NO: 1, or (2) a base sequence selected from the group consisting of nucleotides 255 to 430 of SEQ ID NO: 1, nucleotides 255 to 717 of SEQ ID NO: 1, nucleotides 717 to 1133 of SEQ ID NO: 1, nucleotides 1133 to 1389 of SEQ ID NO: 1, nucleotides 255 to 1857 of SEQ ID NO: 1, nucleotides 571 to 2270 of SEQ ID NO: 1, nucleotides 717 to 2270 of SEQ ID NO: 1, nucleotides 1133 to 2270 of SEQ ID NO: 1, nucleotides 1389 to 2270 of SEQ ID NO: 1, and nucleotides 1634 to 2270 of SEQ ID NO: 1; and ii. a DNA consisting of a base sequence encoding a reporter molecule inserted downstream of the human UCP-2 promoter; and c. a host animal cell line.

3. The kit of claim 2, wherein the reporter molecule is a luciferase.

* * * * *